United States Patent
Aerts et al.

(10) Patent No.: US 10,557,001 B2
(45) Date of Patent: Feb. 11, 2020

(54) COMPOSITE MATERIAL AND RESIN COMPOSITION CONTAINING METASTABLE PARTICLES

(71) Applicant: CYTEC INDUSTRIES INC., Princeton, NJ (US)

(72) Inventors: Vincent Aerts, Wrexham (GB); James Martin Griffin, Orange, CA (US); Judith Elder, Gateshead (GB)

(73) Assignee: CYTEC INDUSTRIES INC., Princeton, NJ (US)

( * ) Notice: Subject to any disclaimer, the term of this patent is extended or adjusted under 35 U.S.C. 154(b) by 157 days.

(21) Appl. No.: 15/753,441

(22) PCT Filed: Aug. 24, 2016

(86) PCT No.: PCT/US2016/048264
§ 371 (c)(1),
(2) Date: Feb. 19, 2018

(87) PCT Pub. No.: WO2017/035175
PCT Pub. Date: Mar. 2, 2017

(65) Prior Publication Data
US 2018/0244873 A1    Aug. 30, 2018

Related U.S. Application Data

(60) Provisional application No. 62/208,974, filed on Aug. 24, 2015.

(51) Int. Cl.
*C08J 5/04* (2006.01)
*C08L 81/04* (2006.01)
*G01N 25/48* (2006.01)

(52) U.S. Cl.
CPC ............... *C08J 5/042* (2013.01); *C08J 5/043* (2013.01); *C08L 81/04* (2013.01); *C08J 2300/22* (2013.01);
(Continued)

(58) Field of Classification Search
CPC .......... C08L 63/00; C08L 77/02; C08L 77/06; C08L 81/06; C08L 81/04; B29C 70/02;
(Continued)

(56) References Cited

U.S. PATENT DOCUMENTS

| 2014/0135443 A1 | 5/2014 | Aerts et al. |
| 2014/0162518 A1* | 6/2014 | Shimizu ..................... C08J 5/24 442/175 |
| 2015/0166743 A1 | 6/2015 | Restuccia et al. |

FOREIGN PATENT DOCUMENTS

EP     2738202 A1    6/2014

OTHER PUBLICATIONS

Catalogue of "TROGAMID® CX, Transparent polyamides with an outstanding combination of properties", Evonik Industries, Mar. 2009.

* cited by examiner

*Primary Examiner* — Camie S Thompson
(74) *Attorney, Agent, or Firm* — Thi Dang

(57) ABSTRACT

A curable matrix resin composition containing a thermoset resin component and metastable thermoplastic particles, wherein the metastable thermoplastic particles are particles of semi-crystalline thermoplastic material with an amorphous polymer fraction that will undergo crystallization upon heating to a crystallization temperature Tc. A fiber-reinforced polymeric composite material containing metastable thermoplastic particles is also disclosed.

20 Claims, 8 Drawing Sheets

(52) U.S. Cl.
CPC ....... *C08J 2300/24* (2013.01); *G01N 25/4866* (2013.01)

(58) Field of Classification Search
CPC ..... B29C 70/025; B29C 70/88; B29C 70/882; C08G 59/32; C08G 59/3227; C08G 59/40; C08J 5/24; C08J 5/10; C08J 5/005; C08J 2300/22; C08J 2300/24; C08J 2363/00; C08J 5/042; C08J 5/043; C08J 5/046; Y10T 156/10; Y10T 428/254; B33Y 70/00; B32B 2260/023; B32B 2260/046; B32B 2262/0269; B32B 2262/101; B32B 2262/106; B32B 2264/0214; B32B 2264/0264; B32B 2307/30; B32B 2307/306; B32B 2307/552; B32B 2307/558; B32B 2307/702; B32B 2307/704; B32B 2307/734; B32B 2419/00; B32B 2605/08; B32B 2605/18; B32B 5/02; B32B 5/024; B32B 5/26
USPC ............... 156/60; 427/385.5; 428/327, 297.4
See application file for complete search history.

COMPOSITE MATERIAL AND RESIN COMPOSITION CONTAINING METASTABLE PARTICLES

CROSS-REFERENCE TO RELATED APPLICATIONS

The present application is a U.S. national phase entry under 35 U.S.C. § 371 of International Application No. PCT/US2016/048264, filed on 24 Aug. 2016, which claims priority to U.S. provisional Application No. 62/208,974, filed on 24 Aug. 2015, the entire content of each of these applications is explicitly incorporated herein by reference.

Fiber-reinforced polymeric (FRP) composite materials have been used in the manufacturing of load-bearing components such as those for aerospace, aeronautical, marine, automotive, and building/construction applications. Conventional matrix materials for FRP composite materials include thermoset resins such as epoxy resins, which are known for their thermal and chemical resistance. Such thermoset resins also display good mechanical properties upon curing but they frequently lack toughness and tend to be very brittle. This is especially true when their crosslinked density is high.

In general terms, the mechanical performances of the cured composite are a function of the individual properties of the reinforcing fibre and the matrix resin, and the interaction between these two components.

DETAILED DESCRIPTION

Figure 1:
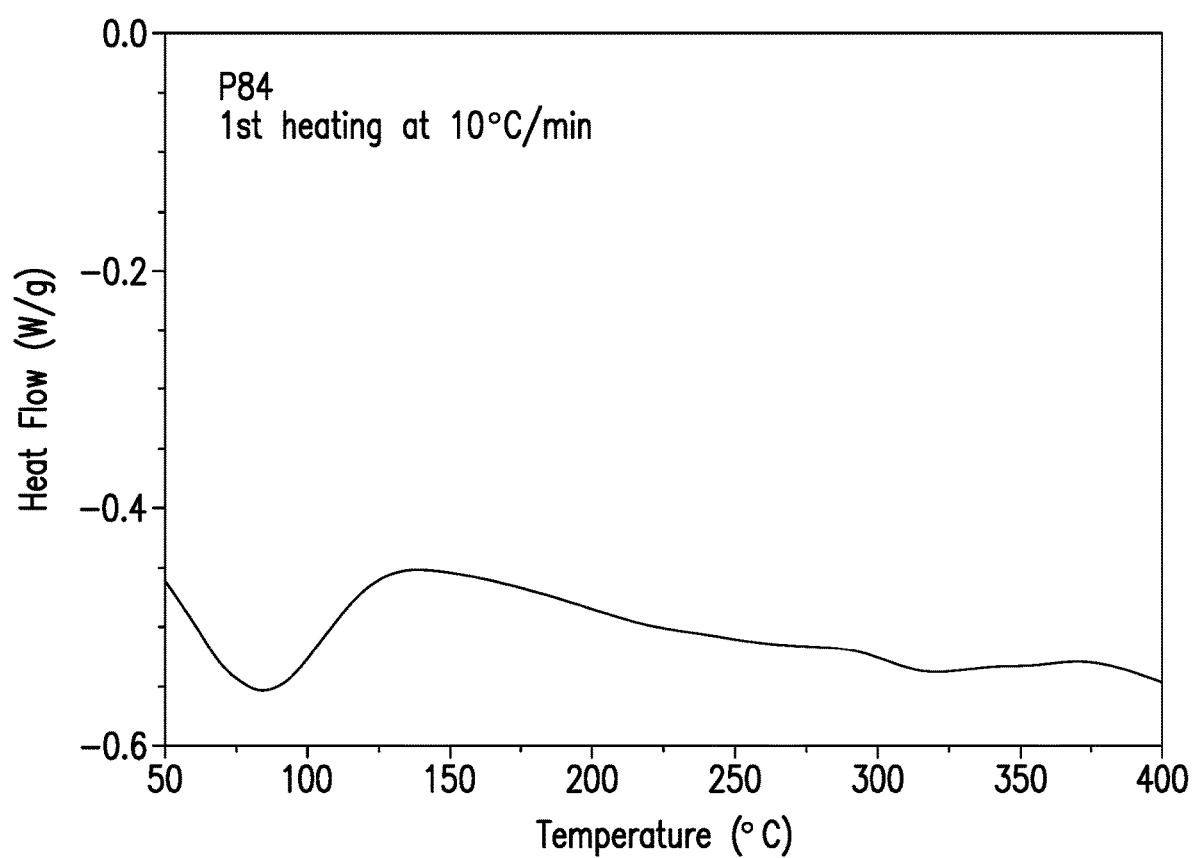
FIG. 1 shows the differential scanning calorimetry (DSC) thermogram of an amorphous polyimide powder, P84®.
Figure 2:
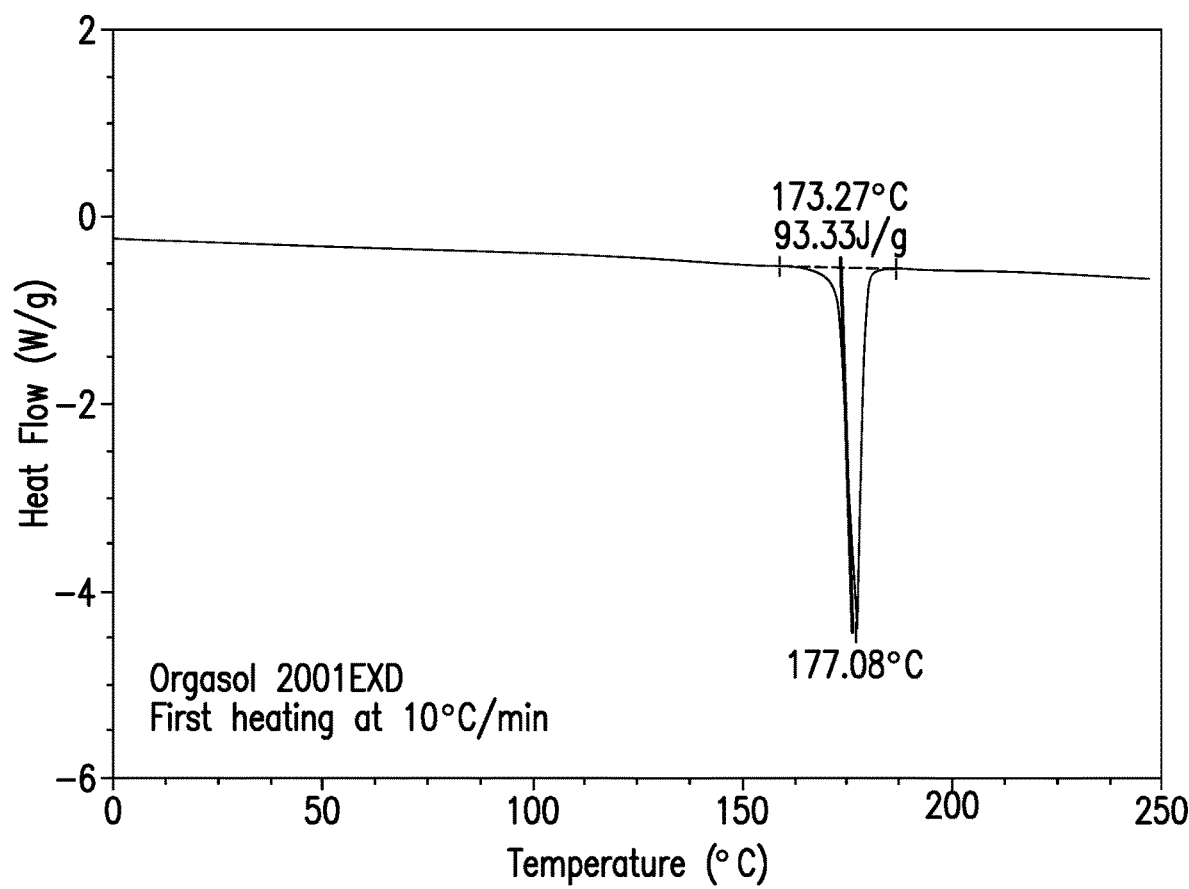
FIG. 2 shows the DSC thermogram of a semi-crystalline polyamide powder, Orgasol® 2001EXD.
Figure 3:
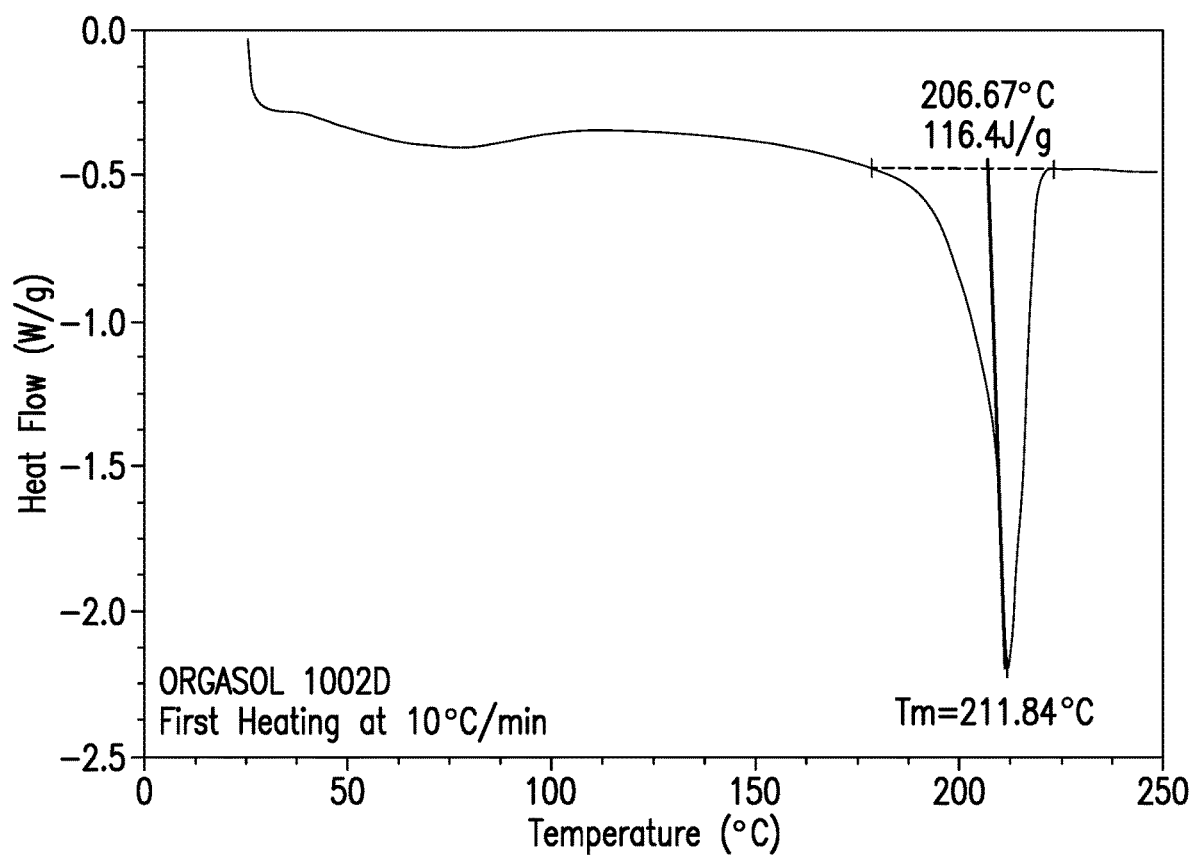
FIG. 3 shows the DSC thermogram of a semi-crystalline polyamide powder, Orgasol® 1002D.
Figure 4:
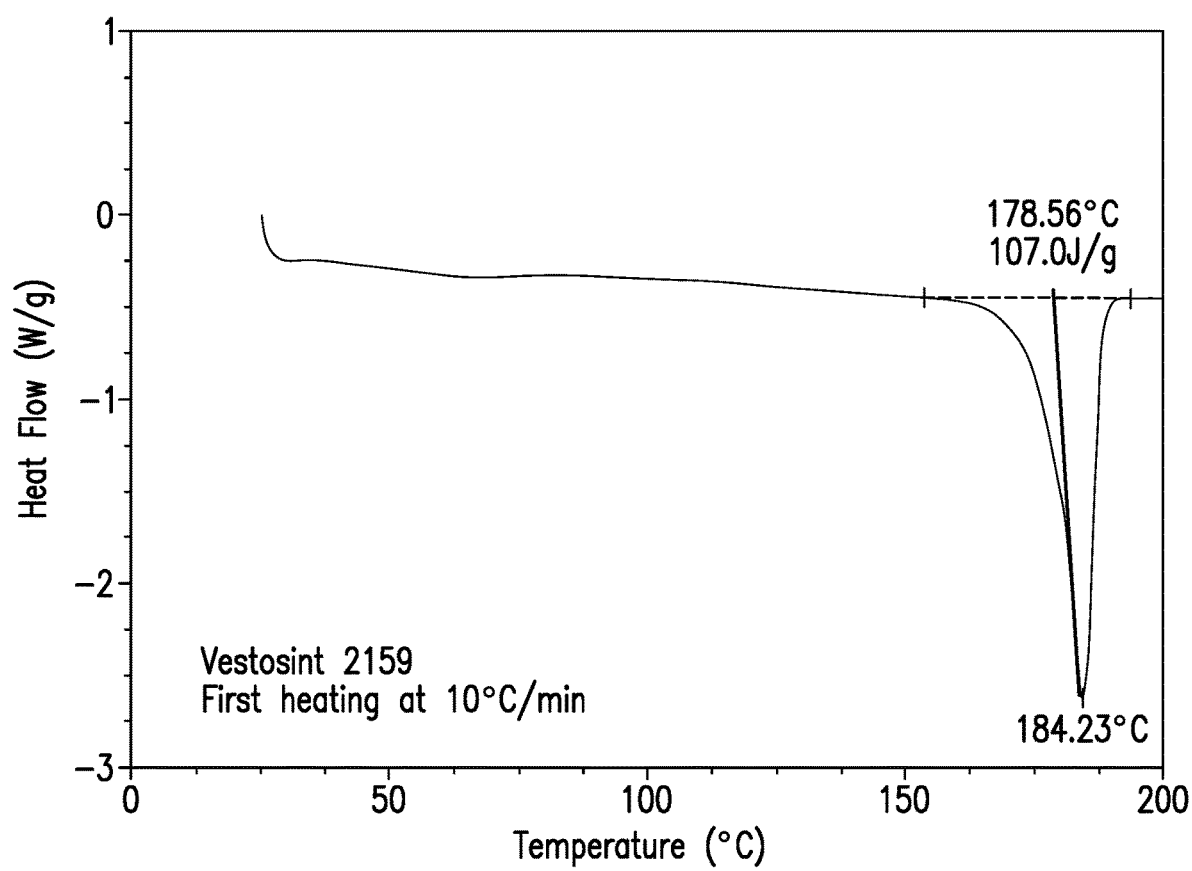
FIG. 4 shows the DSC thermogram a semi-crystalline polyamide, Vestosint® 2159.
Figure 5:
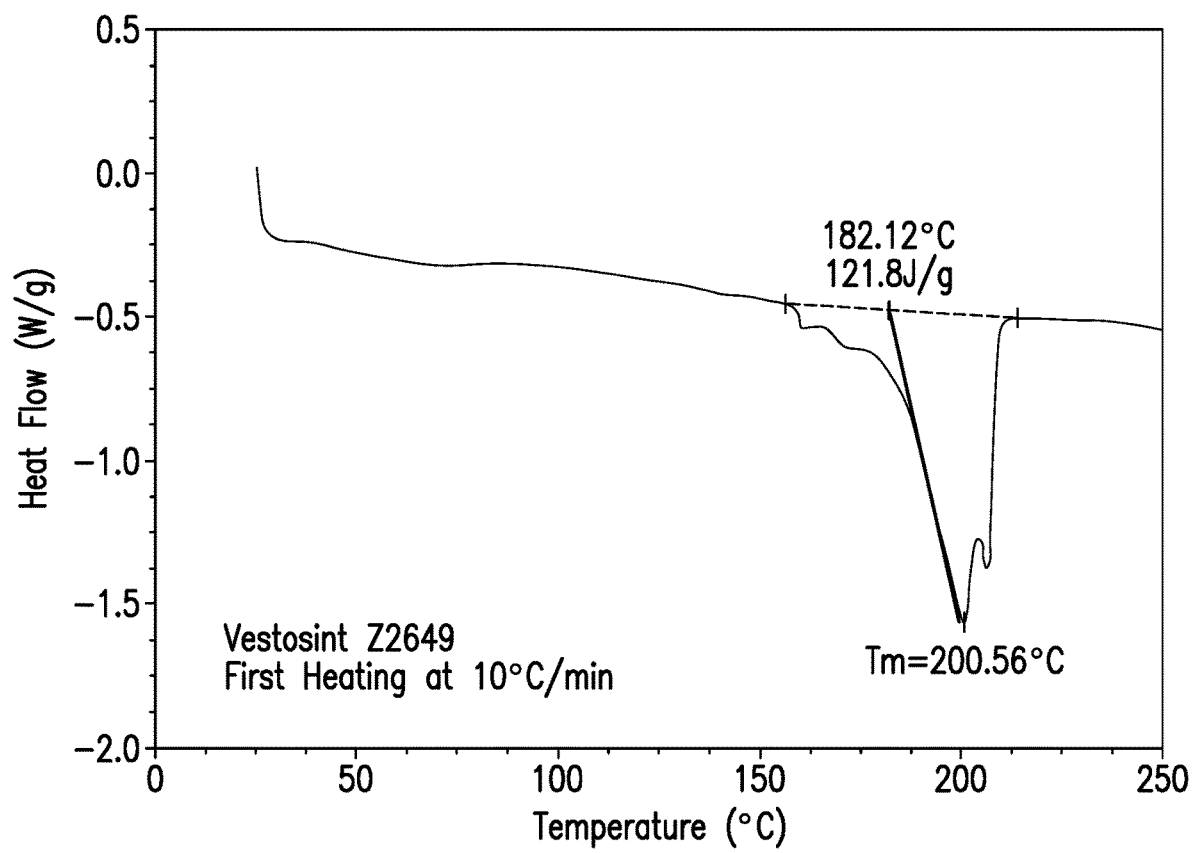
FIG. 5 shows the DSC thermogram of a semi-crystalline polyamide powder based on a polyamide-10,10, Vestosint® Z2649.

Fiber-reinforced polymeric composite materials have been used as the materials for critical load-bearing structures including, but are not limited to, wings and fuselage, which require simultaneously high specific strength, impact resistance, and damage tolerance.

Conventional methods for producing fiber-reinforced composite materials include impregnating continuous reinforcing fibers with a curable matrix resin to form prepregs. This method is often called a "prepregging" method. High-performance structures, e.g. primary and secondary structures of aircrafts and automotive body parts, may be formed by laying up multiple layers of prepregs on a mold surface followed by consolidation and curing.

Due to the pronounced damage sensitivity of cured fiber-reinforced polymer composites, especially when compared to metals such as aluminium, their impact resistance, typically measured by their residual compression strength after impact (CSAI) as well as their damage tolerance, typically measured by their interlaminar fracture toughness in mode I and mode II ($G_{Ic}$ and $G_{IIc}$, respectively) are mechanical performances considered in the design of critical load-bearing composites structures so that such structures are capable of withstanding impacts at energies level likely to be encountered during their service life. A typical impact energy/cured laminate thickness ratio used to evaluated cured composites impact resistance is 1,500 in-lb/in or 6.7 J/mm To ensure the durability of cured composites structures during their service life, a further desirable property of cured composites is their resistance to thermal cycling, also referred to as thermal fatigue resistance. For example, the temperature on an aircraft skin can reach up to 70° C. when parked idle on a runway while it will go down as low as −55° C. when flying at cursing altitude. During a plane life cycle, cured composites parts including, but are not limited to, wings and fuselage, will be subjected to multiple thousands of hot/cold thermal cycles between 70° C. and −55° C. These thermal cycles generate significant internal thermal stresses, which can lead to either matrix cracking or interfacial de-bonding of cured composites containing a multi-component matrix resin. The term "interfacial de-bonding" refers to the de-bonding between two discrete components within the matrix resin, for example, thermoplastic particle and the surrounding thermoset resin, resulting from the thermal stress generated at their interface over the repeated hot/cold thermal cycles. Such thermal stresses originate from a mismatch between the respective coefficients of thermal expansion (CTE) of the two components. Thermal matrix cracking or interfacial de-bonding is commonly referred to as "micro-cracking". Micro-cracking tends to be associated with reduced fatigue resistance and reduced fluid resistance because the presence of micro-cracks increases the percolation pathways for liquids, for example, solvents.

Another important property of cured composites is their resistance to solvents, especially those typically used during cleaning or paint stripping operations. A typically solvent used to evaluate cured composites solvent resistance is methyl ethyl ketone (MEK). MEK has the detrimental effect of plasticizing the matrix resin and reducing its modulus. MEK resistance of cured composites is typically evaluated by measuring the reduction in their in-plane shear modulus (IPSM) after exposure to MEK. A reduction in in-plane shear modulus as low as possible is desirable.

In many applications, particularly aerospace and automotive applications, it is desirable to maximise impact resistance (CSAI) and/or damage tolerance ($G_{1c}/G_{2c}$) while maintaining durability, including thermal cycling resistance (micro-cracking resistance) and solvent resistance (IPSM knockdown as low as possible after exposure to MEK). Increasing CSAI and/or $G_{Ic}$ and $G_{IIc}$, can usually be achieved through the use of thermoplastic toughening particles dispersed within the thermoset matrix resin. However, the presence of certain types of particles may lead to a decrease in micro-cracking resistance and/or a decrease in MEK resistance.

For example, the use of swellable polyimide particles can provide cured composites with high CSAI and micro-cracking resistance, but it has some limitation in damage tolerance, particularly in mode II. While the use of some semi-crystalline polyamide particles can provide cured composites with high CSAI and damage tolerance, the cured composites suffer from micro-cracking during thermal cycling. The use of amorphous polyamide particles can provide cured composites with high CSAI and damage tolerance, and good resistance to micro-cracking during thermal cycling, the cured composites suffer from lower solvent resistance.

To address the design requirements for critical load-bearing structures, there remains a need for composites materials having high impact resistance (CSAI) and damage tolerance ($G_{1c}/G_{2c}$) combined with robust durability, including resistance to micro-cracking during hot/cold thermal cycling and good solvent resistance to sustain the multiple cleaning and paint stripping operations encountered during the structures life cycle. Such composite materials would be highly desirable for aerospace and automotive applications.

A curable resin composition and a fiber-reinforced polymeric composite material containing metastable thermoplastic particles are disclosed. Also disclosed are methods for making composite structures.

In one embodiment, the curable resin composition contains:
  a. a thermoset resin component comprising one or more thermoset resin(s);
  b. metastable thermoplastic particles; and
  c. optionally, a curing agent for the thermoset resin component.
  wherein the metastable thermoplastic particles are particles of semi-crystalline thermoplastic material with an amorphous polymer fraction that will undergo crystallization when the particles are heated to a crystallization temperature $T_c$.

In one embodiment, the fiber-reinforced polymeric composite material includes:
  two or more layers of reinforcement fibers impregnated or infused with a curable thermoset matrix resin;
  metastable thermoplastic particles positioned between adjacent layers of reinforcement fibers,
  wherein the metastable thermoplastic particles are particles of semi-crystalline thermoplastic material with an amorphous polymer fraction that will undergo crystallization when the particles are heated to a crystallization temperature $T_c$.

It has been found that the incorporation of semi-crystalline thermoplastic particles, in their "metastable" state rather than in their usual semi-crystalline stable state, in fiber-reinforced polymeric composite materials can maintain or improve impact resistance and damage tolerance while reducing or eliminating the micro-cracking issues typically encountered with semi-crystalline polyamide particles. Also, the use of such metastable thermoplastic particles as tougheners in composite materials can result in cured composites with improved solvent resistance as compared to the same composites toughened with amorphous polyamide particles.

A key attribute of the metastable thermoplastic particles is the presence of an amorphous polymer fraction within the particle in addition to a crystalline polymer fraction, wherein the amorphous polymer fraction undergoes cold crystallization upon application of heat during the manufacture of cured composite structures. As such, the metastable particles are in a chemically stable state at ambient temperature (20° C.-25° C.), but become thermodynamically unstable state upon heating and undergo cold crystallization. "Cold crystallization" refers to crystallization occurring when a polymer is heated up from room temperature. This terminology is used by people skilled in the art to distinguish it from crystallization occurring when a polymer is cooled down from its molten state to room temperature or lower. In one embodiment, the amorphous polymer fraction which undergoes crystallization upon heating is greater than five percent of the crystalline polymer fraction. In some embodiments, the temperature range in which the amorphous fraction in the metastable thermoplastic particles will undergo crystallization is about 80° C. to the curing temperature $T_{cure}$. In some embodiments the $T_{cure}$ range is about 100° C. to about 250° C., including about 170° C. to about 190° C.

"Curing" or "cure" in this disclosure refers to the hardening of a polymeric material by the chemical cross-linking of the polymer chains. The term "curable" means that the composition is capable of being subjected to conditions which will render the composition to a hardened or thermoset state.

In one embodiment, the metastable particles are particles of polyamides, which may be aliphatic, cyclo-aliphatic, aromatic or any combination thereof. In other embodiments, the metastable particles are particles of other semi-crystalline thermoplastic polymers which are water-insoluble and will undergo cold crystallization upon application of heat during the manufacture of the cured composites structures, for example, polyimide (PI), polyphenylene sulphide (PPS), and polyarylether ketone (PAEK), which includes polyetherether ketone (PEEK), and polyetherether ketone (PEKK).

Metastable Thermoplastic Particles

As used herein, the term "metastable thermoplastic particles" refers to a particulate thermoplastic polymer characterized simultaneously by an endothermic melting enthalpy ($\Delta H_m$) above zero and an exothermic crystallization enthalpy ($\Delta H_c$) above zero. The term "semi-crystalline thermoplastic particles" refers to a particulate thermoplastic polymer characterized simultaneously by an endothermic melting enthalpy ($\Delta H_m$) strictly above zero and an exothermic crystallization enthalpy ($\Delta H_c$) equal to zero. And the term "amorphous thermoplastic particles" refers to a particulate thermoplastic polymer characterized simultaneously by an endothermic melting enthalpy ($\Delta H_m$) equal to zero and an exothermic crystallization enthalpy ($\Delta H_c$) equal to zero. The metastable state of a thermoplastic particle can be quantified by differential scanning calorimetry (DSC) thermogram acquired at a heating rate of 10° C./min under nitrogen atmosphere. The term "particles" as used herein include a powder of fine dry particles with an average diameter below 75 microns as measured by laser scattering using a laser scattering particle size distribution analyzer.

The term "crystallization temperature ($T_c$)" refers to the temperature of the first exothermic peak and the term "crystallization enthalpy ($\Delta H_c$)" refers to the integral of the exothermic peak present in the DSC thermogram acquired at 10° C./min under nitrogen. The presence of such an exothermic peak indicates the presence of an amorphous polymer fraction within the particle that is susceptible to crystallization. The term "melting temperature ($T_m$)" refers to the temperature of the endothermic peak, and the term "melting enthalpy ($\Delta H_m$)" refers to the integral of the endothermic peak present in the DSC thermogram acquired at 10° C./min under nitrogen.

Those skilled in the art will recognize that amorphous thermoplastic particles will display neither an exothermic crystallization peak nor an endothermic melting peak when heated to a temperature range above 50° C., e.g. 51° C.-250° C. FIG. 1 shows the DSC thermogram of an amorphous polyimide powder P84® supplied by HP Polymers, acquired at 10° C./min under nitrogen.

Conventional semi-crystalline polyamide particles, which are in a stable state at ambient temperatures (20° C.-25° C.), do not display any exothermic crystallization peak when heated to a temperature range above 50° C., e.g., 51° C.-250° C., and instead, only show an endothermic melting peak. FIGS. 2-5 show the DSC thermograms, acquired at 10° C./min under nitrogen, of several commercially available, semi-crystalline polyamide powders, respectively: Orgasol® 2001EXD and Orgasol® 1002D, both supplied by Arkema; Vestosint® 2159 and Vestosint® Z2649, both supplied by Evonik Industries.

In contrast, the metastable polyamide particles, according to preferred embodiments of the present disclosure, display both, firstly an exothermic crystallization peak followed by a second endothermic melting peak when heated to a temperature range above about 50° C., e.g., 51° C. to 250° C. These exothermic and endothermic peaks may be fully resolved or may somehow overlap.

Figure 6:
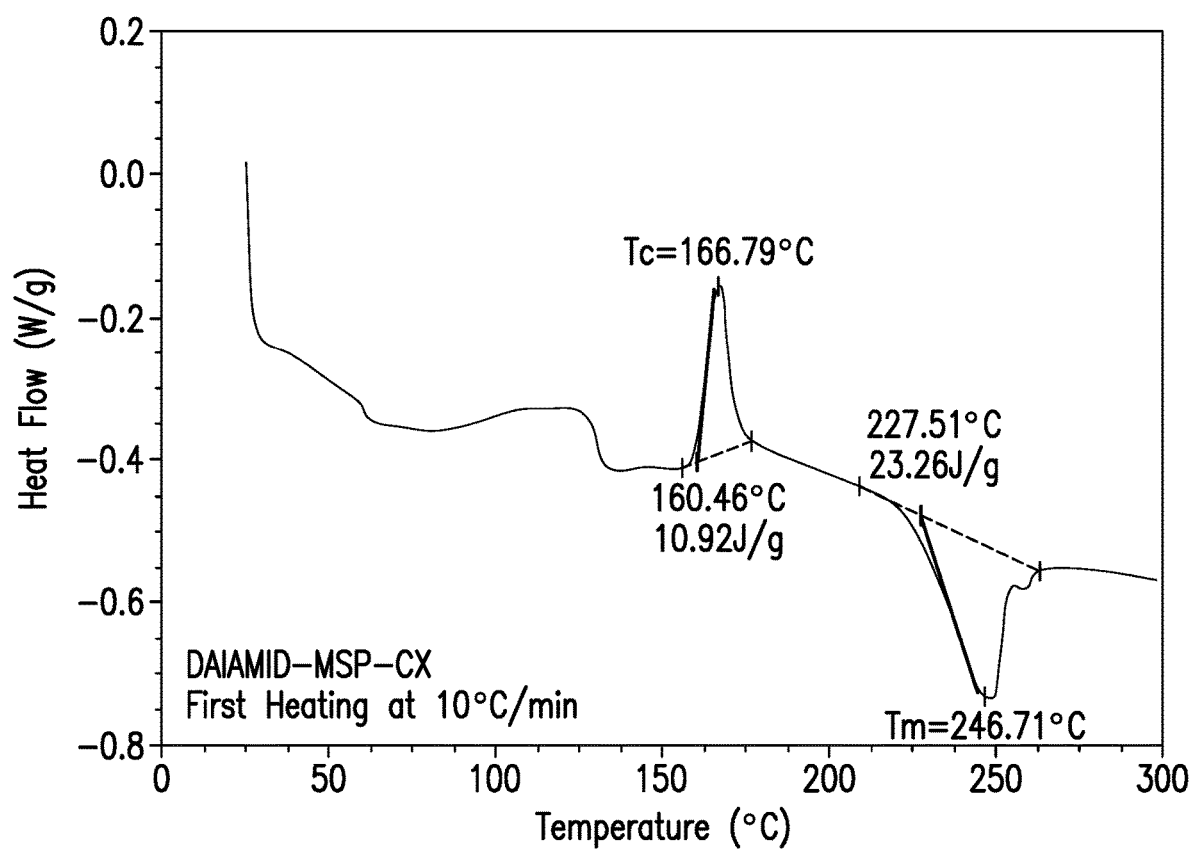
FIG. 6 shows the DSC thermogram for a polyamide powder of semi-cycloaliphatic polyamide, DAIAMID MSP-CX, which was found to be metastable.

FIG. 6 shows the DSC thermogram for a polyamide powder of semi-cycloaliphatic polyamide, DAIAMID® MSP-CX supplied by Evonik, which particles were found to be metastable when heated to a temperature range above 50° C.

Figure 7:
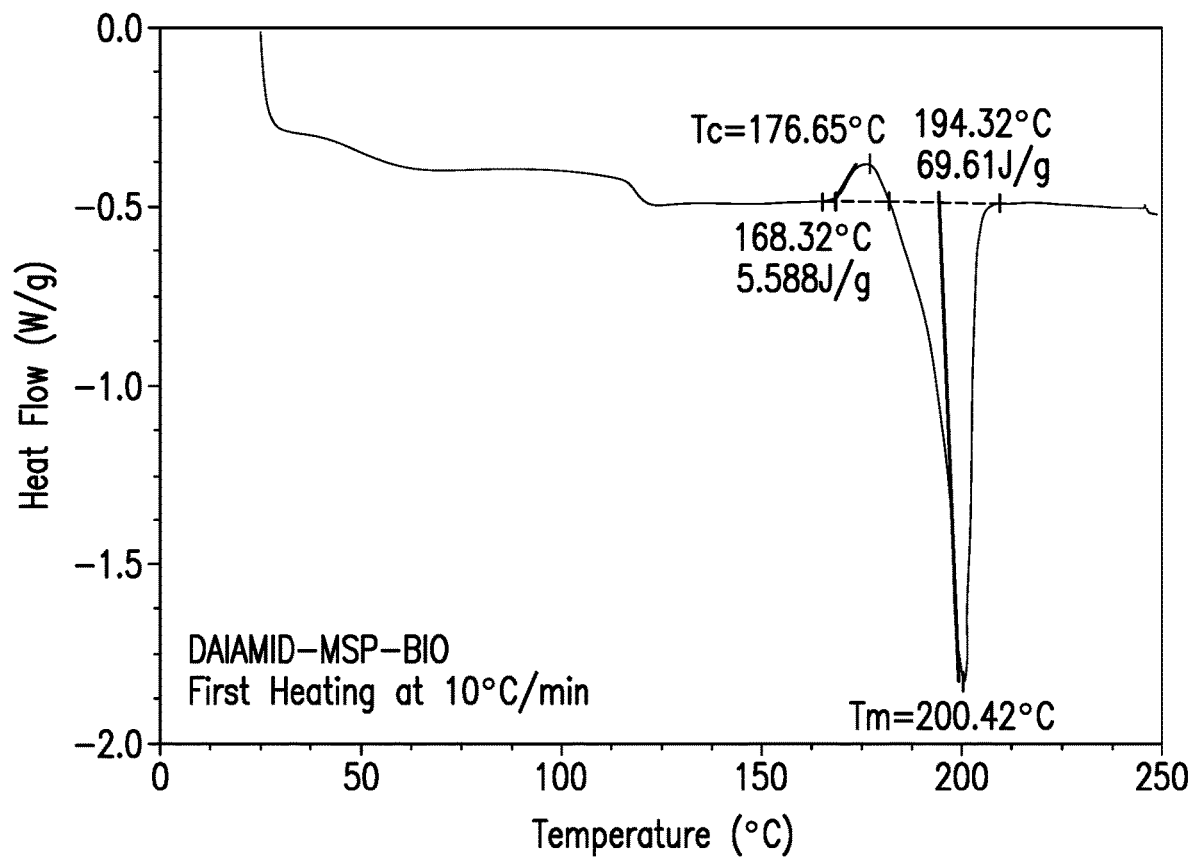
FIG. 7 shows the DSC thermogram of a polyamide powder based on polyamide-10,10 (PA10,10), DAIAMID MSP-BIO, which was found to be metastable.

FIG. 7 shows the DSC thermogram of another metastable polyamide powder based on polyamide-10,10 (PA10,10), DAIAMID® MSP-BIO, sold commercially for cosmetic applications by Daicel-Evonik, which particles were found to be metastable when heated to a temperature range above 50° C.

The metastable particles, which are semi-crystalline, have a crystallization temperature $T_c$ at which the amorphous polymer fraction will undergo crystallization. The metastable particles also have a melting temperature $T_m$. The resin component, curing agent, and metastable particles in the curable resin composition are selected such that the metastable thermoplastic particles undergo further crystallization at a temperature ($T_c$) that is above about 50° C. but below the matrix resin's curing temperature ($T_{cure}$), and such that the melting temperature ($T_m$) of the metastable particles is above the matrix resin's $T_{cure}$ to avoid melting of particles during the cure cycle of the matrix resin. The matrix resin's $T_{cure}$ may range from about 100° C. to about 250° C. $T_c$ may be above about 80° C., including, above about 140° C., provided that $T_c<T_{cure}$. In some embodiments, $T_c$ is in the range of about 100° C. to about 200° C. In some embodiments, $T_{cure}$ may be within the range of about 170° C. to about 190° C., and in some embodiments, $T_{cure}$ is about 180° C.

The metastable particles may be present at a content of about 2.5% to about 30% by weight, including about 5% to about 25%, based on the total weight of the resin composition (i.e., the total weight of the thermoset resin(s), the metastable particles, the curing agent(s) and any optional additional toughening agent(s) or other additives).

Matrix Resin

The one or more thermoset resins in the curable resin composition disclosed herein may include, but are not limited to, epoxy resins, bismaleimide, vinyl ester resins, cyanate ester resins, isocyanate modified epoxy resins, phenolic resins, benzoxazines, formaldehyde condensate resins (such as with urea, melamine or phenol), polyesters, acrylics, and combinations thereof.

Suitable epoxy resins include polyglycidyl derivatives of aromatic diamine, aromatic mono primary amines, aminophenols, polyhydric phenols, polyhydric alcohols, polycarboxylic acids. Examples of suitable epoxy resins include polyglycidyl ethers of the bisphenols such as bisphenol A, bisphenol F, bisphenol S and bisphenol K; and polyglycidyl ethers of cresol and phenol based novolacs.

Specific examples are tetraglycidyl derivatives of 4,4'-diaminodiphenylmethane (TGDDM), resorcinol diglycidyl ether, triglycidyl-p-aminophenol, triglycidyl-m-aminophenol, bromobisphenol F diglycidyl ether, tetraglycidyl derivatives of diaminodiphenylmethane, trihydroxyphenyl methane triglycidyl ether, polyglycidylether of phenol-formaldehyde novolac, polyglycidylether of o-cresol novolac or tetraglycidyl ether of tetraphenylethane.

Commercially available epoxy resins suitable for use in the host resin matrix include N,N,N',N'-tetraglycidyl diamino diphenylmethane (e.g. MY 9663, MY 720, and MY 721 from Huntsman); N,N,N',N'-tetraglycidyl-bis(4-aminophenyl)-1,4-diiso-propylbenzene (e.g. EPON 1071 from Momentive); N,N,N',N'-tetraclycidyl-bis(4-amino-3,5-dimethylphenyl)-1,4-diisopropylbenzene, (e.g. EPON 1072 fromMomentive); triglycidyl ethers of p-aminophenol (e.g. MY 0510 from Hunstman); triglycidyl ethers of m-aminophenol (e.g. MY 0610 from Hunstman); diglycidyl ethers of bisphenol A based materials such as 2,2-bis(4,4'-dihydroxy phenyl) propane (e.g. DER 661 from Dow, or EPON 828 from Momentive, and Novolac resins preferably of viscosity 8-20 Pas at 25° C.; glycidyl ethers of phenol Novolac resins (e.g. DEN 431 or DEN 438 from Dow); di-cyclopentadiene-based phenolic novolac (e.g. Tactix 556 from Huntsman); diglycidyl 1,2-phthalate (e.g. GLY CEL A-100); diglycidyl derivative of dihydroxy diphenyl methane (Bisphenol F) (e.g. PY 306 from Huntsman). Other epoxy resins include cycloaliphatics such as 3',4'-epoxycyclohexyl-3,4-epoxycyclohexane carboxylate (e.g. CY 179 from Huntsman).

Generally, the matrix resin contains one or more thermoset resins in combination with other additives such as curing agents, curing catalysts, co-monomers, rheology control agents, tackifiers, inorganic or organic fillers, elastomeric toughening agents, toughening core-shell particles, stabilizers, inhibitors, pigments, dyes, flame retardants, reactive diluents, soluble or particulate thermoplastics and other additives well known to those skilled in the art for modifying the properties of the resin matrix before or after curing.

The matrix resin composition may be cured by any conventional means, for example, autoclave or infra-red or microwave radiation, and is thermally curable. The addition of one or more curing agent(s) increases the cure rate and/or reduces the cure temperatures. In one embodiment, one or more catalyst(s) may also be used.

The curing agent is suitably selected from known curing agents, for example, aromatic or aliphatic amines, or guanidine derivatives. An aromatic amine curing agent is preferred, preferably an aromatic amine having at least two amino groups per molecule, and particularly preferable are diaminodiphenyl sulphones, for instance where the amino groups are in the meta- or in the para-positions with respect to the sulphone group. Particular examples are 3,3'- and 4-,4'-diaminodiphenylsulphone (DDS); methylenedianiline; bis(4-amino-3,5-dimethylphenyl)-1,4-diisopropylbenzene; bis(4-aminophenyl)-1,4-diisopropylbenzene; 4,4'methylenebis-(2,6-diethyl)-aniline (MDEA from Lonza); 4,4'methylenebis-(3-chloro, 2,6-diethyl)-aniline (MCDEA from Lonza); 4,4'methylenebis-(2,6-diisopropyl)-aniline (M-DIPA from Lonza); 3,5-diethyl toluene-2,4/2,6-diamine (D-ETDA 80 from Lonza); 4,4'methylenebis-(2-isopropyl-6-methyl)-aniline (M-MIPA from Lonza); 4-chlorophenyl-N,N-dimethyl-urea (e.g. Monuron); 3,4-dichlorophenyl-N, N-dimethyl-urea (e.g. Diuron™) and dicyanodiamide (e.g. Amicure™ CG 1200 from Pacific Anchor Chemical).

Suitable curing agents also include anhydrides, particularly polycarboxylic anhydrides, such as nadic anhydride, methylnadic anhydride, phthalic anhydride, tetrahydrophthalic anhydride, hexahydrophthalic anhydride, methyltetrahydrophthalic anhydride, endomethylenetetrahydrophtalic anhydride, and trimellitic anhydride.

Preferably, the amount of thermoset resin component in the resin composition is in the range of from about 20% to about 80%, more preferably in the range of from about 30% to about 70%, relative to the total weight of the resin composition.

The curing agent(s) may be present at a stoichiometry such that there is sufficient amount of reactive groups from the curing agent to react with the reactive groups of the thermoset resin(s), for example, in the range from 0.5 to 1.5 mole of curing agent(s) per mole of the thermoset resin(s).

More generally, the curing agent(s) may be present at about 5% to about 60% by weight, including about 15% to about 50% by weight, and about 20 to about 40% by weight, relative to the combined weight of the thermoset resin component plus curing agent(s) in the resin composition.

Composite Materials

The metastable thermoplastic particles of the present disclosure may be used as interlaminar toughening particles between fibre-reinforcement layers of a composite laminate. In a preferred embodiment, the composite laminate is consisting of multiple layers of reinforcement fibers impregnated or infused with a curable matrix resin (uncured or not fully cured) and metastable particles dispersed in the interlaminar regions formed between adjacent layers of reinforcement fibers. Upon curing of the composite laminate, the metastable particles undergo further crystallization as discussed above. The "interlaminar region" refers to the region between adjacent layers of reinforcing fibers in a multilayered composite structure.

For fabricating high-performance composite materials, suitable reinforcement fibers may be characterized in general terms as having the tensile strength of greater than 500 ksi (or 3447 MPa. Fibers useful for this purpose include carbon or graphite fibres, glass fibers and fibers formed of silicon carbide, alumina, titania, boron and the like, as well as fibers formed from organic polymers such as for example polyolefins, poly(benzothiazole), poly(benzimidazole), polyarylates, poly(benzoxazole), aramid, polyaryl ethers and the like, and may include mixtures having two or more such fibres. Preferably, the fibers are selected from glass fibres, carbon fibres and aramid fibres, such as the fibers sold by the DuPont Company under the trade name KEVLAR. The fibers may be used in the form of continuous tows made up of multiple filaments, as sheet of continuous unidirectional fibers, as woven fabric or nonwoven multiaxial fabrics. The woven form may be selected from a plain, satin, or twill weave style. The multiaxial forms may have a number of plies and fibre orientations, for example, non-crimp fabrics.

The metastable particles may be present at a content of about 2.5% to about 30% by weight based on the total resin content in the composite material, and in some embodiment, about 5% to about 25%.

In certain embodiments, the metastable particles may be used in combination with other interlaminar toughening particles, which may be polymeric (e.g. polyimide, polyarylsulphone, elastomers) or inorganic (e.g., carbon, metallic). In some embodiments, the interlaminar region is void of any thermoplastic particles that melt prior to the curing temperature $T_{cure}$ of the matrix resin. When other particles are present, the total amount of particles may be up to about 25% by weight based on the total resin content of the composite material.

Method of Making Metastable Polymer Particles

The metastable polymer particles of the present disclosure may be manufactured by a solvent-free melt process, whereby the manufacturing process inhibits the development of full and stable crystallinity so as to preserve them in a "metastable" state.

As an example, the solvent-free melt process may include:

a) extruding a molten mixture of a water-insoluble thermoplastic resin (e.g. polyamide resin) in amorphous state and a water-soluble matrix material using an extruder, such as single-screw extruder or twin-screw extruder, to form a molten resin composition, in the form of strands or sheets, containing fine particles of thermoplastic resin dispersed in the water-soluble matrix material;

b) cooling and solidifying the molten resin composition under such conditions to prevent recrystallization, for example, cooling and solidifying may be carried out quickly; and c) dissolving and removing the water-soluble material from the solidified resin composition by washing with water to thereby yield fine spherical particles of metastable semi-crystalline thermoplastic polymer.

The ratio of the thermoplastic resin to the water-soluble matrix material in the molten mixture during the extruding step may be about 1/99 to about 60/40 by weight, preferably about 5/95 to about 50/50 by weight.

The sizes (dimensions) of the fine particles can be controlled, for example, by adjusting conditions or parameters such as the type of the water-soluble material, the ratio of the thermoplastic resin to the water-soluble material, the melting temperature, the structure of the screw(s) in the extruder, and the rotation rate of the screw(s).

The resin composition just extruded from the extruder is in a molten state, in which the fine thermoplastic particles and the matrix material are both melted or softened before cooling and solidifying. The extruded resin exiting from the die of the extruder is deposited onto a conveying device, such as a belt conveyer, that moves horizontally in an extrusion direction below the die of the extruder at a position that is not so far from holes of the die. The conveying device is moving at a speed substantially equal to the extrusion speed of the extruder, and the extruded resin composition is cooled by air and thereby solidified. The conveying device may be cooled by a cooling device. The cooling temperature in air cooling is, for example, about 0° C. to about 35° C.

The water-soluble matrix material is preferably a water-soluble material that can be softened at the same molten/softening temperature as that of the water-insoluble thermoplastic resin, for example, at about 100° C. to 300° C., that can be kneaded with the water-insoluble thermoplastic resin, and that can separate from the water-insoluble thermoplastic resin into two phases in a molten or solidified state. Examples of such water-soluble materials are saccharides including monosaccharides, oligosaccharides, polysaccharides, sugar alcohols, polydextroses, maltodextrin, and inulin; hydrogenated products and hydrolyzed products of these saccharides; and water-soluble resins. The hydrogenated products and hydrolyzed products of the saccharides include hydrogenated hexoses, hydrogenated disaccharides, hydrogenated starches, invert sugar, and hydrogenated or non-hydrogenated decomposed products of starches. Each of these water-soluble materials can be used alone or in combination.

Examples of the monosaccharides are xylose, ribulose, glucose, mannose, galactose, fructose, and sorbose. The polysaccharides are saccharides containing eleven or more molecules of one or more monosaccharides and/or sugar alcohols being bonded through glycoside linkages as a result of dehydrative condensation. Examples thereof are inulin, achrodextrin, polydextrose, amylose, amylopectin, starches, and celluloses. The sugar alcohols include, for example, erythritol, pentaerythritol, arabitol, ribitol, xylitol, sorbitol, mannitol, and galactitol. Examples of the water-soluble resins are linear polymers intramolecularly having a hydrophilic group such as —CONH—, —COOH, or —OH, including polyacrylamides, poly(acrylic acid)s, poly(methacrylic acid)s, poly(itaconic acid)s, and poly(vinyl alcohol)s.

Examples of the oligosaccharides are disaccharides such as trehalose, maltose, isomaltose, isomaltulose, maltitol, cellobiose, gentiobiose, lactose, lactitol, sucrose, 1,6-GPS (6-O-a-D-glucopyranosyl-D-sorbitol), 1,1-GPS (1-O-a-D-glucopyranosyl-D-sorbitol), and 1,1-GPM (1-O-a-D-glucopyranosyl-D-mannitol); trisaccharides such as cellotriose, gentianose, maltotriose, and raffinose; tetrasaccharides such as lycotetraose, maltotetraose, and stachyose; pentasaccharides such as maltopentaose and verbascose; hexasaccharides such as maltohexaose; as well as tri-, tetra- or pentasaccharides such as maltodextrin; and hepta- or octasaccharides such as dextrin's and cyclodextrin.

The washing with water may be conducted by placing the cooled and solidified resin composition in water, and dissolving the water-soluble matrix material in water while stirring. The temperature upon washing with water may be set as appropriate within ranges not adversely affecting the spherical shapes of fine particles and is, for example, about 0° C. to about 100° C. The washing temperature may also be a temperature exceeding 100° C. If necessary, the washing water may include an organic solvent so as to remove water-insoluble impurities.

After washing with water, the fine spherical thermoplastic resin particles can be recovered by subjecting the aqueous dispersion which contains fine spherical thermoplastic resin particles of the water-insoluble thermoplastic resin dispersed in water to a conventional separation process such as filtration or centrifugal separation, followed by drying.

The resulting fine, substantially spherical thermoplastic resin particles may have an average particle diameter (or size) of about 0.01 μm to about 100 μm, including about 5 μm to about 75 μm. The average particle size can be determined by using a laser scattering particle size distribution analyzer, e.g. a Mastersizer from Malvern.

Methods of Making Composite Materials and Structures

The composite materials and structures with interlaminar metastable particles of the present disclosure may be manufactured using different processes.

Each fiber layer may be separately impregnated/infused with a matrix resin to form a prepreg. The term "prepreg" as used herein includes a sheet or layer of fibers that has been pre-impregnated with a resin matrix within at least a portion of their volume. The resin matrix may be present in a partially cured or uncured state. The prepregs may be fully impregnated prepregs or partially impregnated prepregs. Typically, a prepreg is in a form that is ready for molding and curing into the final composite part and is commonly used in manufacturing load-bearing structural parts, such as wings, fuselages, bulkheads and control surfaces of aircrafts. Important properties of the cured prepregs are high strength and stiffness with reduced weight.

A plurality of prepreg plies may be laid up in a stacking sequence to form a "prepreg lay-up." Each prepreg ply may contain unidirectionally aligned fibers and the prepreg plies within the layup may be positioned so that the unidirectional fibers are in a selected orientation with respect to one another, e.g. 0°, ±45°, 90°, etc. Prepreg lay-ups may be manufactured by techniques that may include, but are not limited to, hand lay-up, automated tape laydown (ATL), advanced fibre placement (AFP), and filament winding.

In one embodiment, the particles are deposited onto the surface of a prepreg ply prior to laminating multiple prepreg plies together to form a laminated stack that is ready for curing. The particles may be deposited via any conventional techniques such as sprinkling, electrostatic deposition, scatter coating, spray distribution, and any other technique known by a person skilled in the art. The distributed composite particles adhere to the surface of the prepreg due to the tack of the resin. When the prepreg plies are stacked together to form a laminate panel, the particles remain in the interlaminar regions of the laminate panel.

In another embodiment, a specific amount of the particles are mixed with the curable/uncured matrix resin prior to the prepreg manufacturing. In such embodiment, resin films are manufactured first by coating a particle-containing resin mixture onto a release paper. Then, the resulting resin film is laminated onto a layer of fibers under the aid of heat and pressure to impregnate the fibres, thereby forming a prepreg ply with specific fibre areal weight and resin content. During the resin film lamination process, the particles are filtered and remain external to the fibre layer due to the fact that the size of the particles is larger than the spacing between the fibres. Subsequently, when two layers of prepregs containing particles are laminated one on top of the other, the particles are positioned in the interlaminar region between two adjacent prepreg plies.

In an alternative embodiment, a curable resin composition without particles is coated onto a release paper to form a resin film, which is then brought into contact with one or both opposing surfaces of a fiber layer. The resin impregnates the fibers and leaves a little or no resin on the external surfaces of the fibre layer. Subsequently, a second film of curable resin containing particles is brought into contact with an outer surface of the resin-impregnated fiber layer. An additional film of curable resin containing the particles may be brought into contact with the opposite outer surface of the resin-impregnated fibre layer to form a sandwich structure. As a result, a particle-containing resin layer remains outside of the impregnated fibre layer and does not further impregnate the fibres. A plurality of such structures are laminated together to form a composite structure with particles positioned in the interlaminar regions.

In another embodiment, two films of curable resin composition without particles are brought into contact with the two opposing surfaces of a fiber layer. The resin impregnates the fibers and leaves little or no resin on the external surfaces of the fiber layer. Subsequently, two films of curable resin containing particles are brought into contact with the opposing surfaces of the pre-impregnated fiber layer. A plurality of such structures are laminated together to form a composite panel with particles in the interlaminar regions. Such approach is preferred as it tends to provide a well-ordered laminate resulted from the particles not disrupting the placement of the fibres.

The composite materials, structures or prepregs formed by the above methods may be in the form of tapes, towpregs, or webs, with continuous or chopped fibres.

In another embodiment, the metastable particles are incorporated in a fibrous preform configured for receiving liquid resin via resin infusion process such as RTM and VaRTM.

The preform consists of multiple layers of dry reinforcement fibers with the particles interposed between adjacent layers of dry reinforcement fibers. The layers of dry reinforcement fibers are permeable to liquid resin.

The layers of reinforcement fibers in the preform may be any type of textiles known in the prior art for manufacturing composite materials. Examples of suitable fabric types or configurations include, but are not limited to: all woven fabrics, examples are plain weave, twill weave, sateen weave, spiral weave, and uni-weave; all multiaxial fabrics, examples of which include, warp-knitted fabrics, and non-crimp fabrics (NCF); knitted fabrics; braided fabrics; all non-woven fabrics, examples of which include, but are not limited to, mat fabrics composed of chopped and/or continuous fiber filaments, felts, and combinations of the aforementioned fabric types.

In a resin infusion process, the preform is positioned in a mold, which is injected with a curable liquid resin to wet out the fiber layers. The matrix resin for RTM and VaRTM systems must possess a very low injection viscosity to allow complete wetting and infusion of the preform.

In some embodiments, the cured composite displays simultaneously the following properties:
a) excellent or improved impact resistance, particularly residual compression strength after an impact of 1500 in-lb/in (CSAI);
b) excellent or improved damage tolerance, particularly interlaminar fracture toughness in mode I and mode II, without significant detriment to durability;
c) minimal or no micro-cracking in the interlaminar region;
d) excellent solvent resistance; and
e) excellent or improved hot wet open holed compression strength (HW OHC).

EXAMPLES

In the following examples, the mechanical performances of the composites were measured according to the following techniques.

Inter-laminar fracture toughness in mode I ($G_{1c}$) was measured in inch-pound per square inches (in-lb/in$^2$) on double-cantilevered beam (DCB) coupons as described in ASTM D5528. A uni-directional (UD) layup containing 26 plies was used to manufacture coupon of 10" in length by 1" in width. A release film was placed at on edge of the coupon in the mid plane to create a 2.5" in length delamination crack starter. The DCB coupons were then loaded in tension until delamination growth. The interlaminar fracture toughness in mode I ($G_{1c}$) is the critical value of the strain energy release rate (G) associated with the onset of delamination growth in mode I. The values of $G_{1c}$ were calculated according to the modified beam theory by using Equation 1, where $F_{max}$ is the maximum recorded load at the onset of delamination growth, w is the coupon width, and ∂C/∂a is the partial derivative of the coupon compliance (∂C) for an infinitesimal delamination crack growth (∂a).

$$G_{1c}=(F_{max})^2/(2w)\partial C/\partial a \text{ [in-lb/in}^2] \quad \text{Equation 1}$$

Interlaminar fracture toughness in mode II ($G_{2c}$) was measured in inch-pound per square inches (in-lb/in2) on end-notched flexural (ENF) coupons via as described in ASTM D7905. A uni-directional (UD) layup containing 26 plies was used to manufacture coupon of 10" in length by 1" in width. A release film was placed at on edge of the coupon in the mid plane to create a 2.5" in length delamination crack starter. The ENF coupons were then loaded in 3-point bend until delamination growth. The inter-laminar fracture toughness in mode II ($G_{2c}$) is the critical value of the strain energy release rate (G) associated with the onset of delamination growth in mode II. The values of $G_{2c}$ were by using Equation 2, where $F_{max}$ is the maximum recorded load at the onset of delamination growth, w is the coupon width, a is the crack length, C is the coupon compliance, and L is half the loading span.

$$G_{2c}=(9a^2F^2_{max}C)/(2w(2L^3+3a^3)) \text{ [in-lb/in}^2] \quad \text{Equation 2}$$

Compression strength after impact (CSAI) was measured in kilo-pounds per square inches (ksi) on three times symmetrical quasi-isotropic layups ($[+45/0/-45/90]_{3s}$) as described in ASTM D7136 and ATSM D7137. The coupons of 6" in length by 4" in width were subjected to an impact energy of 270 inch-pound (in-lb) prior to being tested. This impact energy was selected in order to obtain an impact energy/cured laminate thickness ratio of 1,500 in-lb/in. The values of CSAI were calculated by using Equation 3, where $F_{max}$ is the maximum load, w is the coupon width, and t is the coupon thickness.

$$\text{CSAI}=F_{max}/(w\cdot t) \text{ [ksi]} \quad \text{Equation 3}$$

In-plane shear modulus (IPSM) was measured in mega-pounds per square inches (Msi) on symmetrical cross-ply layups ($[+45/-45]_s$) as described in BSS7320. The coupons were loaded in tension until an axial strain of 0.5%. The values of IPSM were calculated by using Equation 4, where $E_x$ is the axial secant modulus measured between the origin and 0.4% axial strain, and mu is the Poisson's ratio measured at 0.4% axial strain.

$$\text{IPSM}=E_x/(2(1+mu)) \text{ [Msi]} \quad \text{Equation 4}$$

To evaluate the resistance to methyl ethyl ketone (MEK), additional IPSM coupons were immersed in MEK at room temperature for six days before being tested as per the procedure described above. An MEK knockdown factor was calculated as a percentage decrease in IPSM following the MEK exposure by using Equation 5, where IPSM is the value measured on unconditioned coupons and $\text{IPSM}_{MEK}$ is the value measured on coupons immersed for six days in MEK.

$$\text{MEK knockdown}=(\text{IPSM}-\text{IPSM}_{MEK})/\text{IPSM} \text{ [\%]} \quad \text{Equation 5}$$

To evaluate thermal cycling resistance, 2 in ×3 in coupons of a two times symmetrical quasi-isotropic layups ($[+45/0/-45/90]_{2s}$) were cycled for 2,000 times between −54° C. and 71° C. The coupons were then cross-sectioned and polished prior to being imaged by optical microscopy. The number of micro-crack per square millimetre was then counted.

Hot wet open hole compression strength (HW OHC) was measured in kilo-pounds per square inches (ksi) on two times symmetrical quasi-isotropic layups ($[+45/0/-45/90]_{2s}$) as described in ASTM D6484. The coupons of 12" in length by 1.5" in width with a 0.25" hole in the centre were subjected to an immersion in water at 160 F (71 C) for 14 days prior to being tested at 180 F (82 C). The values of HW OHC were calculated by using Equation 6, where $F_{max}$ is the maximum load, w is the coupon width, and t is the coupon thickness.

$$\text{HW OHC}=F_{max}/(w\cdot t) \text{ [ksi]} \quad \text{Equation 6}$$

Materials

Araldite® MY0510 is a triglycidyl p-aminophenol and Araldite®®® PY306 is a diglycidyl ether of bisphenol-F, both from Huntsman.

Sumikaexcel™ 5003P is a polyethersulphone from Sumitomo Chemical,

Aradur 9664-1 is 4,4'-diaminodiphenyl sulphone (4,4'-DDS) from Huntsman,

DAIAMID® MSP BIO is product name for semi-crystalline particles based on polyamide-10,10 (PA10,10), having an average particle size of 8.6 μm, produced according to the Solvent-Free® melt process, supplied by Evonik Industries.

Vestosint® Z2654 is product name for semi-crystalline particles based on polyamide-10,10 (PA10,10), having an average particle size of 16.1 μm, and produced by a solvent-free melt process, supplied by Evonik Industries.

Trogamid® MSP A7042 is product name for particles of semi-cycloaliphatic polyamide which is a product of cycloaliphatic diamines and dodecanedioic acid, having an average particle size of 15.8 μm, produced by a solvent-free melt process, supplied by Evonik Industries.

Vestosint® Z2649 is product name for particles of semi-crystalline polyamide-10,10 (PA10,10) having an average particle size of 10.4 μm, supplied by Evonik Industries.

Orgasol® 2001EXD is product name for particles of semi-crystalline polyamide-12 (PA12), having an average particle size of 10.0 μm, supplied by Arkema.

Orgasol® 1002D is product name for particles of semi-crystalline polyamide-6 (PA6), having an average particle size of 19.6 μm, supplied by Arkema.

Vestosint® 2159 is product name for particles of semi-crystalline polyamide-12 (PA12), having an average particle size of 10.9 μm, supplied by Evonik Industries.

Fortron® 0205B4 is product name for ground particles of semi-crystalline polyphenyle sulfide (PPS), having an average particle size of 20.0 μm, supplied by Ticona.

P84 is product name for ground particles of amorphous polyimide, having an average particle size of 44 μm, supplied by HP Polymers.

DAIAMID® MSP-CX is product name for particles of semi-cycloaliphatic polyamide, which is a product of cycloaliphatic diamines and dodecanedioic acid, having an average particle size of 16.9 μm, produced according to a solvent-free melt process, supplied by Evonik Industries.

All particle sizes were determined by laser scattering technique.

Example 1

A resin system U without toughening particles was formulated using the components shown in Table 1.

TABLE 1

| Component | Units | Resin U |
| --- | --- | --- |
| Araldite MY0510 | weight % | 27.6 |
| Araldite PY306 | weight % | 27.6 |
| Aradur 9664-1 | weight % | 27.3 |
| Sumikaexcel 5003P | weight % | 17.5 |

Resin U was prepared by mixing the epoxy precursors Araldite®® MY0510 and Araldite®® PY306 at a temperature ranging between 60° C. and 90° C. Sumikaexcel 5003P (polyethersulphone) was added to the epoxy mixture and then dissolved at a temperature ranging between 110° C. and 130° C. Aradur 9664-1 (4,4'-DDS) was then added and mixed at a temperature ranging between 60° C. and 90° C.

The resin U so produced was then filmed to a nominal aerial weight of 23.4 gsm (gram per square meter) on a release paper. Intermediate modulus carbon fibres were spread in a conventional prepreg machine to form a fiber web of unidirectional fibers with a nominal aerial weight of 190 gsm. The formed fiber web was then sandwiched between two films of resin U to obtain a prepreg U with a nominal fiber areal weight (FAW) of 190 gsm, and a nominal resin content of 19.8% by weight.

Six resin compositions P.1-P.6 containing different thermoplastic particles were formulated using the components shown in Table 2. All amounts are in weight %.

TABLE 2

| Components | | Resin P.1 | Resin P.2 | Resin P.3 | Resin P.4 | Resin P.5 | Resin P.6 |
| --- | --- | --- | --- | --- | --- | --- | --- |
| Araldite ® MY0510 | | 21.1 | 21.2 | 21.3 | 21.2 | 21.4 | 20.7 |
| Araldite ® PY306 | | 21.2 | 21.2 | 21.3 | 21.2 | 21.4 | 20.7 |
| Aradur ® 9664-1 | | 21.0 | 21.0 | 21.5 | 21.0 | 21.1 | 0.5 |
| Sumikaexcel ™ 5003P | | 13.4 | 13.4 | 13.5 | 13.4 | 13.5 | 13.2 |
| Thermoplastic particles | Particle Code | | | | | | |
| DAIAMID ® MSP BIO (Metastable particles) | E-P1 | 23.2 | 0 | 0 | 0 | 0 | 0 |
| Vestosint ® Z2654 (Metastable particles) | E-P2 | 0 | 23.2 | 0 | 0 | 0 | 0 |
| Trogamid ® MSP A7042 (Metastable particles) | E-P3 | 0 | 0 | 22.4 | 0 | 0 | 0 |
| Vestosint ® Z2649 | C-P4 | 0 | 0 | 0 | 23.2 | 0 | 0 |
| Orgasol ® 2001EXD | C-P5 | 0 | 0 | 0 | 0 | 22.6 | 0 |
| Orgasol ® 1002D | C-P6 | 0 | 0 | 0 | 0 | 0 | 24.9 |

Each resin composition in Table 2 was prepared by mixing the epoxy precursors Araldite®® MY0510 and Araldite® PY306 at a temperature ranging between 60° C. and 90° C. Sumikaexcel 5003P (polyethersulphone) was added and then dissolved at a temperature ranging between 110° C. and 130° C. Aradur 9664-1 (4,4'-DDS) was then added and mixed at a temperature ranging between 60° C. and 90° C.

Each resin composition P so produced was then filmed to a nominal areal weight of 23.4 gsm onto a release paper. Using a conventional prepreg machine, the prepreg U formed as described above was sandwiched between two resin films formed from the particle-containing resin composition P to obtain a prepreg P having a nominal fibre areal weight (FAW) of 190 gsm and a total nominal resin content of 33% by weight.

A plurality of prepregs P was laid up to form a composite laminate. The laminate was enclosed in a conventional zero-bleed, sealed vacuum bag and cured in an autoclave for 2 hours at 180° C. under a pressure of 85 psi while maintaining the vacuum throughout the cure cycle. The different toughening particles that were used are labelled as E-P1, E-P2, E-P3, C-P4, C-P5, and C-P6 in Table 2.

The cured panels were then tested for damage resistance testing (CSAI), and fracture toughness in mode I ($G_{1c}$) and mode II ($G_{2c}$). The results are reported in Table 3.

Particles C-P5 (Orgasol® 2001EXD) are characterized by the absence of crystallization, a $T_m$ of 177.08 C and a $\Delta H_m$ of 93.33 J/g as determined by DSC at a heating rate of 10° C./min under nitrogen atmosphere. They are characterized by a ratio of $\Delta H_c/\Delta H_m$ of 0% since there is no crystallization peak. Orgasol 2001EXD did not undergo crystallization during the cure of the composite laminate but did undergo

TABLE 3

| Property | Units | Examples | | | Counter examples | | |
|---|---|---|---|---|---|---|---|
| | | E-P1 | E-P2 | E-P3 | C-P4 | C-P5 | C-P6 |
| Thermoplastic particle | — | Metastable | Metastable | Metastable | Semi-crystalline | Semi-crystalline | Semi-crystalline |
| CSAI 30 J impact | ksi | 51.3 | 45.7 | 50.8 | 43.1 | 36.9 | 44.2 |
| | (MPa) | (353.71) | (315.10) | (350.27) | (297.17) | (254.43) | (304.76) |
| $G_{1c}$ | in-lb/in² | 4.2 | 4.1 | 3.4 | 1.9 | 2.6 | 2.1 |
| | (J/m²) | (735) | (717.5) | (595) | (332.5) | (455) | (367.5) |
| $G_{2c}$ | in-lb/in² | 14.1 | 13.7 | 17.6 | 11.1 | 9.3 | 5.9 |
| | (J/m²) | (2467.5) | (2397.5) | (3080) | (1942.5) | (1627.5) | (1032.5) |

Note:
1 ksi = 6.895 MPa and 1 in-lb/in² = 175 J/m².

Metastable Particles E-P1 (DAIAMID® MSP BIO) are characterized by a $T_c$ of 176.65° C., a $\Delta H_c$ of 5.59 J/g, a $T_m$ of 200.42° C., and a $\Delta H_m$ of 69.91 J/g as determined by DSC acquired at a heating rate of 10° C./min under nitrogen atmosphere. They are characterized by a ratio of $\Delta H_c/\Delta H_m$ of 8%. These particles underwent further crystallization during the curing of the composite laminates with no subsequent melting. It was found that these particles yielded simultaneously a high CSAI of 51.3 ksi, a high $G_{1c}$ of 4.2 in-lb/in², and a high $G_{2c}$ of $G_{1c}$ of 14.1 in-lb/in².

Metastable Particles E-P2 (Vestosint® Z2654) are characterized by a $T_c$ of 166.99° C., a $\Delta H_c$ of 11.44 J/g, and a $T_m$ of 246.14° C., and a $\Delta H_m$ of 25.33 J/g as determined by DSC acquired at a heating rate of 10° C./min under nitrogen atmosphere. They are characterized by a ratio of $\Delta H_c/\Delta H_m$ of 45.2%. As such, these particles underwent crystallization during the cure of the composite laminate with no subsequent melting. It was found that these particles yielded simultaneously a high CSAI of 45.7 ksi, a high $G_{1c}$ of 4.1 in-lb/in², and a high $G_{2c}$ of 13.7 in-lb/in².

Metastable Particles E-P3 (Trogamid® MSP A7042) are characterized by a $T_c$ of 166.71° C., a $\Delta H_c$ of 10.60 J/g, a $T_m$ of 245.94° C., and a $\Delta H_m$ of 20.09 J/g as determined by DSC at a heating rate of 10° C./min under nitrogen atmosphere. They are characterized by a ratio of $\Delta H_c/\Delta H_m$ of 52.7%. These particles underwent crystallization during the cure of the laminates at a curing temperature ($T_{cure}$) at 180 C with no subsequent melting. It was found that these particles yielded simultaneously a high CSAI of 50.8 ksi, a high $G_{1c}$ of 3.4 in-ln/in², and a high $G_{1c}$ of $G_{1c}$ of 17.6 in-ln/in².

Particles C-P4 (Vestosint® Z2649) are characterized by a $T_m$ of 200.56° C. and a $\Delta H_m$ of 121.80 J/g as determined by DSC at a heating rate of 10° C./min under nitrogen atmosphere. They are characterized by a ratio of $\Delta H_c/\Delta H_m$ of 0% since there is no crystallization peak. These particles did not undergo crystallization or melting during the cure of the composite laminate. It was found that the semi-crystalline nature of such particles produced lower interaction with the surrounding matrix resin, which resulted in a lower CSAI of 43.1 ksi, a lower $G_{1c}$ of 1.9 in-lb/in², and a lower $G_{2c}$ of 11.1 in-lb/in². When comparing these results with those obtained for metastable particles E-P1 with the same particle chemistry, the advantage of using metastable polyamide particles instead of its semi-crystalline counterpart is apparent.

melting. It was found that the semi-crystalline nature of such particles produced lower interaction with the surrounding matrix resin despite its melting during the cure of the composite laminate, thereby resulting in a lower CSAI of 36.9 ksi, a lower $G_{1c}$ of 2.6 in-lb/in², and a lower $G_{2c}$ of 9.3 in-lb/in². When comparing these results with those obtained for metastable particles E-P1 to E-P3, the advantage of using metastable polyamide particles instead of semi-crystalline polyamide particles having a $T_m$ below $T_{cure}$ is apparent. Furthermore, the use of polyamide particles having a $T_m$ below $T_{cure}$ of the matrix resin is typically associated with a detrimental lack of robustness to cure profiles, particularly when the curing agent 4,4'-DDS is used in an epoxy-based thermoset resin. For example, at slower heating rates such as 0.25° C./min and 0.5° C./min, the resin system presented in Table 1, in which the polyamide particles are embedded, would gel at a temperature $T_{gel}$ of 143° C. and 159° C., respectively. Such gel temperatures are below the C-P5 polyamide particles' melting temperature $T_m$ of 177.08° C., hence, the particulate morphology would be maintained in the cured laminate. At faster heating rates, such as 2° C./min, the resin system presented in Table 1, in which the polyamide particles are embedded, would gel at a temperature $T_{gel}$ of 192° C., which is above the C-P5 polyamide particles' melting temperature $T_m$ of 177.08° C., and as a result, the particles would coalesce in their molten state leading to a coarser and non-particulate morphology. This change in morphology as a function of heating rate causes concerns regarding robustness in mechanical performances as well as fluid resistance.

$T_{gel}$ can be determined by running a viscosity test on an ARES-G2 from TA Instruments at a frequency of 1 Hz using 25 mm diameter parallel plates with a 0.5 mm gap and a 20% strain. The temperature can be ramped up from 70° C. to 200° C. at various heating rates, such as 0.25° C./min, 0.5° C./min, or 2° C./min. The gel temperate $T_{gel}$ is determined as the temperature at which the loss modulus (G") curve crossovers with the elastic modulus (G') curve.

Particles C-P6 (Orgasol® 1002D) are characterized by a $T_m$ of 211.84° C. and a $\Delta H_m$ of 116.04 J/g as determined by DSC at a heating rate of 10° C./min under nitrogen atmosphere. They are characterized by a ratio of $\Delta H_c/\Delta H_m$ of 0% since there is no crystallization peak. Orgasol® 1002D did not undergo crystallization or melting during the cure of the laminates at a curing temperature ($T_{cure}$) at 180° C. Similarly than in the counter example C-P4, it was found that the semi-crystalline nature of such particle gives lower interaction with the surrounding matrix resin results in a lower CSAI of 44.2 ksi, a lower $G_{1c}$ of 2.1 in-lb/in$^2$, and a lower $G_{2c}$ of 5.9 in-ln/in$^2$. When comparing these results with those obtained in examples E-P1 to E-P3, the advantage of using a metastable polyamide instead of a semi-crystalline polyamide having a $T_m$ above $T_{cure}$ is apparent.

Example 2

Six (6) resin compositions (Resins P.3, P.7, P.8, P.9, P.11) containing different thermoplastic particles were prepared according to the formulations shown in Table 4. The procedure for mixing the components of the resin compositions is as described in Example 1. All amounts shown are in weight percentage (%).

TABLE 4

| Components | Particle code | Resin P.3 | Resin P.8 | Resin P.9 | Resin P.11 |
|---|---|---|---|---|---|
| Araldite ® MY0510 | | 21.3 | 21.2 | 19.6 | 19.7 |
| Araldite ® PY306 | | 21.2 | 21.2 | 19.6 | 19.7 |
| Aradur 9664-1 | | 21.5 | 21.0 | 19.8 | 19.7 |
| Sumikaexcel 5003P | | 13.5 | 13.4 | 12.5 | 12.5 |
| Thermoplastic particles | | | | | |
| Trogamid MSP A7042 (Metastable particles) | E-P3 | 22.4 | 0 | 0 | 0 |
| Vestosint ® 2159 | C-P8 | 0 | 23.2 | 0 | 0 |
| Fortron ® 020584 | C-P9 | 0 | 0 | 28.5 | 0 |
| P84 | C-P11 | 0 | 0 | 0 | 28.4 |

Each resin composition was then filmed to a nominal areal weight of 23.4 gsm on a release paper. Using a conventional prepreg machine, the prepreg U formed as described previously in Example 1 was then sandwiched between top and bottom films of resin composition P to obtain a prepreg P with a nominal fibre areal weight (FAW) of 190 gsm and a total nominal resin content of 33% by weight.

A plurality of prepregs P was laid up to form a composite laminate. The laminate was enclosed in a conventional zero-bleed, sealed vacuum bag and cured in an autoclave for 2 hours at 180° C. under a pressure of 85 psi while maintaining the vacuum throughout the cure cycle. The different toughening particles that were used are labelled as E-P3, C-P7, C-P8, C-P9, and C-P11 in Table 4.

The cured panels were then tested for damage resistance (CSAI), fracture toughness in mode I ($G_{1c}$) and mode II ($G_{2c}$), thermal cycling and MEK resistance. The results are reported in Table 5.

TABLE 5

| | | Example | Counter examples | | |
|---|---|---|---|---|---|
| Property | Units | E-P3 | C-P8 | C-P9 | C-P11 |
| Thermoplastic particle | — | Metastable | Semi-crystalline | Semi-crystalline | Amorphous |
| CSAI 30J impact | ksi (MPa) | 50.8 (350.27) | 51.3 (353.71) | 27.6 (190.30) | 44.2 (304.76) |
| $G_{1c}$ | in-lb/in$^2$ (J/m$^2$) | 3.4 (595) | 3.4 (595) | 1.5 (262.5) | 2.1 (367.5) |
| $G_{2c}$ | in-lb/in$^2$ (J/m$^2$) | 17.6 (3080) | 14.9 (2607.5) | 6.2 (1085) | 11.1 (1942.5) |
| Micro-crack after 2,000 cycles | #/mm$^2$ | 0 | 9 | 4 | 0 |
| MEK knockdown | % | 0.6% | 1.7% | 0.6% | 6.4% |
| HW OHC | ksi (MPa) | 42.5 (293) | 37.2 (256) | 42.1 (290) | 36.9 (254) |

Note:
1 ksi = 6.895 MPa and 1 in-lb/in$^2$ = 175 J/m$^2$

Particles C-P8 (Vestosint® 2159) are characterized by the absence of crystallization, a $T_m$ of 184.23° C. and a $\Delta H_m$ of 107.00 J/g as determined by DSC at a heating rate of 10° C./min under nitrogen atmosphere. They are characterized by a ratio of $\Delta H_c/\Delta H_m$ of 0% since there is no crystallization peak. These particles did not undergo crystallization during the cure of the composite laminate. While this semi-crystalline PA12 particle matches the impact resistance and damage tolerance of metastable particles, it was found that the composite containing these semi-crystalline particles suffered from micro-cracking following exposure to thermal cycling. This causes durability concerns and limits the usage of such semi-crystalline polyamides in critical load bearing structures such as aerospace composite parts. In contrast to composite laminate with semi-crystalline PA12 particles, the composite laminate with metastable polyamide particles did not result in micro-cracking after thermal cycling exposure.

Particles C-P9 (Fortron® 0205B4) are semi-crystalline particles with high melting point and are characterized by the absence of crystallization, a $T_m$ of 288.31° C. and a $\Delta H_m$ of 57.17 J/g. As a result, these particles did not undergo crystallization during the cure of the composite laminate. It was found that the composite containing these semi-crystalline particles not only suffered from poor impact resistance and damage tolerance, it also suffered from micro-cracking following exposure to thermal cycling.

Particles C-P11 (P84) are characterized by the absence of crystallization and melting. As a result, these particles did not undergo crystallization during the cure of the composite laminate and also did not undergo any subsequent melting. While P84 particles provided high impact and thermal cycling resistance, metastable polyamide particles have the advantage of providing increased damage tolerance in mode I and II as well as improved MEK and moisture resistance as illustrated by the significantly higher G1c and G2c values as well as the lower IPSM knockdown after exposure to MEK and the higher HW OHC.

Example 3

Two resin systems (Resins F.2 and F.3) were prepared according to the formulations shown in Table 6.

TABLE 6

Resin F formulations

| Component | Particle code | Resin F.2 | Resin F.3 |
|---|---|---|---|
| Araldite ® MY0510 | | 23.0 | 23.0 |
| Araldite ® PY306 | | 23.0 | 23.0 |
| Aradur ® 9664-1 | | 23.4 | 23.4 |
| Sumikaexcel ™ 5003P | | 18.5 | 18.5 |
| Thermoplastic particles | | | |
| Vestosint ® Z2649 | C-P4 | 12.1 | 0 |
| DAIAMID ® MSP-CX (metastable particles) | E-F3 | 0 | 12.1 |

Each resin composition was prepared by mixing the epoxy resins Araldite® MY0510 and Araldite® PY306 at a temperature ranging between 60° C. and 90° C. Sumikaexcel® 5003P was added and then dissolved at a temperature ranging between 110° C. and 130 C. Aradur® 9664-1 was then added and mixed at a temperature ranging between 60° C. and 90° C. The thermoplastic particles were then added and mixed at a temperature between 60° C. and 90° C.

Each resin composition so produced was then filmed to a nominal aerial weight of 51.2 gsm on a release paper. Carbon fibres were spread in a conventional prepreg machine to form a fibres web with a nominal aerial weight of 190 gsm. The so formed fibres web was then sandwiched between top and bottom films of resin F to obtain a prereg F with a nominal fibre areal weight (FAW) of 190 gsm, and a nominal resin content of 35% by weight.

A plurality of prepregs F was laid up to form a composite laminate. The laminate was enclosed in a conventional zero-bleed, sealed vacuum bag and cured in an autoclave for 2 hours at 180° C. under a pressure of 85 psi while maintaining the vacuum throughout the cure cycle.

The cured panels were then tested for damage resistance (CSAI), fracture toughness in mode I ($G_{1c}$) and mode II ($G_{2c}$), and thermal cycling resistance. The results are reported in Table 7.

TABLE 7

| Property | Units | C-P4 | E-F3 |
|---|---|---|---|
| Thermoplastic particles | — | Semi-crystalline | Metastable |
| CSAI 30J impact | ksi | 44.7 | 46.4 |
| | (MPa) | (308.21) | (319.93) |
| $G_{1c}$ | in-lb/in² | 2.5 | 2.9 |
| | (J/m²) | (437.5) | (507.5) |
| $G_{2c}$ | in-lb/in² | 10.0 | 8.7 |
| | (J/m²) | (1750.0) | (1522.5) |
| Micro-cracks after 2,000 cycles | #/mm² | 6.0 | 0.0 |

Note:
1 ksi = 6.895 MPa and 1 in-lb/in² = 175 J/m².

Metastable Particles E-F3 (DAIAMID MSP-CX) are characterized by a $T_c$ of 166.79° C., a $\Delta H_c$ of 10.92 J/g, a $T_m$ of 246.71° C. and a $\Delta H_m$ of 23.26 J/g as determined by DSC at a heating rate of 10° C./min under nitrogen atmosphere. They are characterized by a ratio of $\Delta H_c/\Delta H_m$ of 46.9%. As a result, these particles underwent crystallization during the cure of the composite laminate with no subsequent melting. It was found that, again, the metastable particles yielded a good balance of impact resistance and damage tolerance with no micro-cracking issues during thermal cycling.

While the composite containing particles C-P4 (Vestosint Z2649) matched the composite containing particles E-F3 in impact resistance and damage tolerance performances, the former suffered from micro-cracking during thermal cycling exposure.

Example 4

To further exemplify the use of semi-crystalline thermoplastic particles in their "metastable" state rather than in their usual semi-crystalline stable state, two (2) resin compositions (Resins P.12, P.13) containing different thermoplastic particles were prepared according to the formulations shown in Table 8. The procedure for mixing the components of the resin compositions is as described in Example 1. All amounts shown are in weight percentage (%).

TABLE 8

Resin F formulations

| Component | Particle code | Resin P.12 | Resin P.13 |
|---|---|---|---|
| Araldite ® MY0510 | | 20.33 | 23.0 |
| Araldite ® PY306 | | 20.33 | 23.0 |
| Aradur ® 9664-1 | | 22.24 | 23.4 |
| Sumikaexcel ™ 5003P | | 12.90 | 18.5 |
| Thermoplastic particles | | | |
| DAIAMID ® MSP-CX (metastable particles) | E-F3 | 24.20 | 0 |
| Annealed DAIMID ® MSP-CX | C-P13 | 0 | 24.20 |

Each resin composition was then filmed to a nominal areal weight of 23.4 gsm on a release paper. Using a conventional prepreg machine, the prepreg U formed as described previously in Example 1 was then sandwiched between top and bottom films of resin composition P to obtain a prepreg P with a nominal fibre areal weight (FAW) of 190 gsm and a total nominal resin content of 33% by weight.

Two (2) prepregs P were laid up to form a composite laminate. The laminate was enclosed in a conventional zero-bleed, sealed vacuum bag and cured in an autoclave for 2 hours at 180° C. under a pressure of 85 psi while maintaining the vacuum throughout the cure cycle. The different toughening particles that were used are labelled as E-F3 and C-P13 in Table 8.

The cured panels were then tested for damage resistance (CSAI), fracture toughness in mode I ($G_{1c}$) and mode II ($G_{2c}$). The results are reported in Table 9.

TABLE 9

| | | Examples | |
|---|---|---|---|
| Property | Units | E-F3 | C-P13 |
| Thermoplastic particle | — | Metastable | Semi-crystalline |
| CSAI 30J impact | ksi | 49.7 | 47.2 |
| | (MPa) | (342.68) | (325.44) |
| $G_{1c}$ | in-lb/in² | 4.5 | 2.3 |
| | (J/m²) | (787.5) | (402.5) |
| $G_{2c}$ | in-lb/in² | 14.0 | 15.2 |
| | (J/m²) | (2450) | (2660) |

TABLE 9-continued

| | | Examples | |
|---|---|---|---|
| Property | Units | E-F3 | C-P13 |
| Micro-cracks after 6,000 cycles | #/mm² | 0 | 10 |

Note:
1 ksi = 6.895 MPa and 1 in-lb/in² = 175 J/m²

As in the previous examples, the composite containing particles E-F3 (DAIAMID-MSP-CX) displays high impact resistance and damage tolerance performances.

Figure 8:
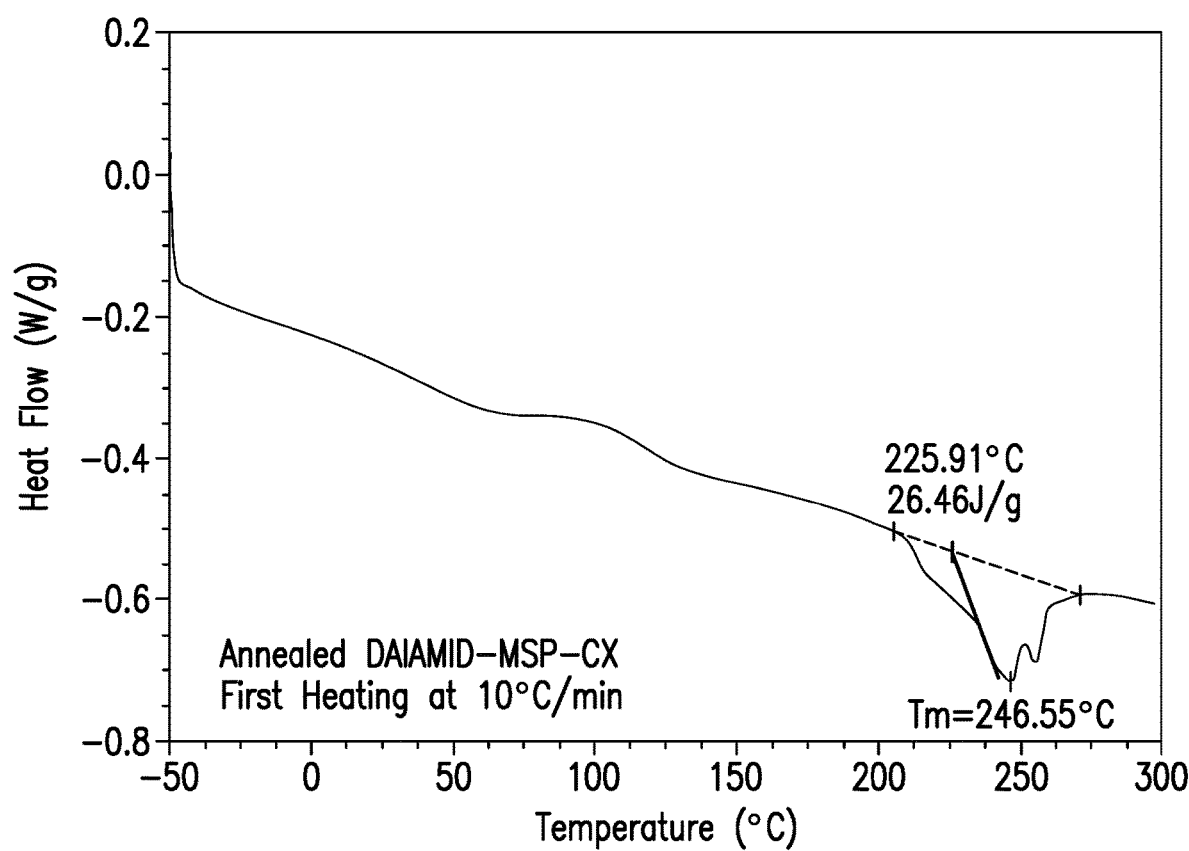
FIG. 8 shows the DSC thermogram for annealed DAI-AMID® MSP-CX polyamide particles.

Particles C-P13 (Annealed DAIAMID MSP-CX) are semi-crystalline particles characterized by the absence of further crystallization, a $T_m$ of 246.55° C. and a $\Delta H_m$ of 26.46 J/g as determined by DSC at a heating rate of 10° C./min under nitrogen atmosphere. The particles C-P13 were obtained by annealing DAIAMID MSP-CX particles at a temperature 20° C. above their crystallization temperature $T_c$ of 166.79° C. for thirty (30) minutes to ensure full crystallization. FIG. 8 shows the DSC thermogram for the annealed DAIAMID MSP-CX particles. As a result, these particles did not undergo crystallization during the cure of the composite laminate. It was found that the composite containing these semi-crystalline particles displayed similar impact resistance and damage tolerance in mode-II ($G_{2c}$) as compared to their metastable counterparts but suffered from a much lower damage tolerance in mode-I ($G_{1c}$). Because $G_{1c}$ performance is a key driver for the durability and fatigue resistance to delamination of composites structures, this significant decrease in $G_{1c}$ (almost 50%) is highly undesirable for high-performance composite structures such as those for aerospace and automotive applications. These results further highlight the benefits of using semi-crystalline thermoplastic particles in their "metastable" state rather than in their conventional semi-crystalline stable state.

The metastable polyamide particles described herein may be used as a single type of interlaminar toughening particles, or in combination with different semi-crystalline polyamide particles characterized by a $T_m$ above $T_{cure}$, or in combination with amorphous thermoplastic particles, to achieve similar damage tolerance in term of CSAI and $G_{2c}$ performances. Thus, the use of low-melting polyamide particles having a $T_m$ below $T_{cure}$ of the matrix resin can be eliminated. The presence of such low-melting polyamide particles is typically associated with a detrimental lack of robustness to cure profiles as discussed above. $G_{1c}$ performance is a key driver for the durability and fatigue resistance to delamination of composites structures. As such, a significant increase in $G_{1c}$ while maintaining similar CSAI and $G_2$ performances is highly desirable for high-performance composite structures such as those for aerospace and automotive applications.

The invention claimed is:

1. A fiber-reinforced polymeric composite material comprising:
   two or more layers of reinforcement fibers impregnated or infused with a curable thermoset matrix resin;
   metastable thermoplastic particles positioned between adjacent layers of reinforcement fibers,
   wherein the metastable thermoplastic particles are particles of semi-crystalline thermoplastic material with an amorphous polymer fraction that will undergo crystallization when the particles are heated to a crystallization temperature $T_c$.

2. The composite material of claim 1, wherein, upon heating to a temperature range of 50° C. to 250° C. at 10° C./min under nitrogen atmosphere, the metastable thermoplastic particles display an exothermic peak followed by an endothermic peak as determined by differential scanning calorimetry (DSC).

3. The composite material of claim 1, wherein the metastable particles are characterized simultaneously by a melting enthalpy ($\Delta H_m$) above zero and a crystallization enthalpy ($\Delta H_c$) above zero as determined by differential scanning calorimetry (DSC),
   wherein $\Delta H_m$ and $\Delta H_c$ are determined by integrating the area under the melting peak and crystallization peak, respectively, present in the DSC thermogram.

4. The composite material according to claim 1, wherein the curable matrix resin has a curing temperature $T_{cure}$, and the metastable particles have a melting temperature ($T_m$) which is above $T_{cure}$.

5. The composite material according to claim 4, wherein $T_c$ is less than $T_{cure}$.

6. The composite material of claim 5, wherein $T_c$ is above 50° C. and $T_{cure}$ ranges from 100° C. to 250° C.

7. The composite material of claim 5, wherein $T_c$ is in the range of 100° C. to 200° C.

8. The composite material according to claim 1, wherein the metastable thermoplastic particles are particles of polyamide.

9. The composite material according to claim 1, wherein the metastable thermoplastic particles are particles of polyphenylene sulphide (PPS) or polyarylether ketone (PAEK).

10. The composite material according to claim 1, wherein the metastable particles are present in an amount of 2.5% to 30% by weight based on the total resin content in the composite material.

11. The composite material according to claim 1, further comprising other polymeric particles or inorganic particles.

12. The composite material according to claim 1, wherein the region between adjacent layers of reinforcement fibers is void of any polymeric particles with a melting temperature below $T_{cure}$.

13. The composite material according to claim 1, wherein the reinforcement fibers are in the form of continuous, unidirectionally aligned fibers, woven fabric or multiaxial fabric.

14. The composite material according to claim 1, wherein the reinforcement fibers are selected from carbon fibers, aramid fibers, glass fibers, and combination thereof.

15. The composite material according to claim 1, wherein the resin component comprises one or more thermoset resin(s) selected from: epoxy resins, bismaleimide, vinyl ester resins, cyanate ester resins, phenolic resins, benzoxazines, formaldehyde condensate resins, unsaturated polyesters, acrylics, and combinations thereof.

16. The composite material according to claim 15, wherein the resin component comprises one or more epoxy resins.

17. A fiber-reinforced polymeric composite material comprising:
   two or more layers of reinforcement fibers impregnated or infused with a curable thermoset matrix resin;
   metastable thermoplastic particles positioned between adjacent layers of reinforcement fibers,
   wherein the metastable thermoplastic particles are particles of semi-crystalline thermoplastic material, wherein the metastable particles are in a chemically stable state at ambient temperature (20° C. to 25° C.), but become thermodynamically unstable when the particles are heated to a crystallization temperature $T_c$.

18. A method of making a composite structure comprising:
forming a composite laminate comprising two or more layers of reinforcement fibers impregnated with a curable thermoset matrix resin and metastable thermoplastic particles positioned between adjacent layers of reinforcement fibers, wherein the metastable thermoplastic particles are particles of semi-crystalline thermoplastic material with an amorphous polymer fraction capable of crystallizing at a crystallization temperature $T_c$; and
curing the composite laminate at a curing temperature $T_{cure}$,
wherein, during ramping up to the curing temperature $T_{cure}$, the metastable thermoplastic particles underwent crystallization at the crystallization temperature $T_c$, which is less than $T_{cure}$.

19. The method of claim 18, wherein $T_c$ is above about 50° C. and $T_{cure}$ is within the range of 100° C. to 250° C.

20. The method of claim 18, wherein the metastable particles have a melting temperature ($T_m$) which is above $T_{cure}$.

* * * * *